US007065399B2

(12) United States Patent
Nakada

(10) Patent No.: US 7,065,399 B2
(45) Date of Patent: Jun. 20, 2006

(54) MUSCLE FATIGUE LEVEL MEASURING DEVICE

(75) Inventor: Masato Nakada, Asaka (JP)

(73) Assignee: Tanita Corporation, Tokyo (JP)

( * ) Notice: Subject to any disclaimer, the term of this patent is extended or adjusted under 35 U.S.C. 154(b) by 301 days.

(21) Appl. No.: 10/697,100

(22) Filed: Oct. 31, 2003

(65) Prior Publication Data

US 2004/0092840 A1    May 13, 2004

(30) Foreign Application Priority Data

Dec. 25, 2002   (JP) ............................. 2002-373574

(51) Int. Cl.
*A61B 5/103* (2006.01)
*A61B 5/117* (2006.01)
*A61B 5/05* (2006.01)

(52) U.S. Cl. ...................................... 600/547; 600/587
(58) Field of Classification Search ................ 600/547, 600/587; 33/511, 512
See application file for complete search history.

(56) References Cited

U.S. PATENT DOCUMENTS

| 4,667,513 | A | * | 5/1987 | Konno ...................... 73/379.01 |
| 5,335,667 | A | * | 8/1994 | Cha et al. .................... 600/547 |
| 6,185,451 | B1 | * | 2/2001 | Richardson et al. ......... 600/546 |
| 6,468,232 | B1 | * | 10/2002 | Ashton-Miller et al. .... 600/591 |
| 6,516,222 | B1 | * | 2/2003 | Fukuda ........................ 600/547 |
| 6,714,814 | B1 | * | 3/2004 | Yamada et al. .............. 600/547 |
| 2004/0082877 | A1 | * | 4/2004 | Kouou et al. ................ 600/546 |
| 2004/0167386 | A1 | * | 8/2004 | Kasahara et al. ........... 600/382 |

FOREIGN PATENT DOCUMENTS

| EP | 1 114 610 | 7/2001 |
| JP | 06-304157 | 11/1994 |
| JP | P2000-232 A | 1/2000 |
| JP | P2002-224072 A | 8/2002 |

\* cited by examiner

*Primary Examiner*—Max F. Hindenburg
*Assistant Examiner*—Matthew D. Dryden
(74) *Attorney, Agent, or Firm*—McDermott Will & Emery LLP

(57) ABSTRACT

A muscle fatigue level measuring device is provided which estimates muscle fatigue without being influenced by distances between electrodes. The muscle fatigue level measuring device measures a resistance component and a reactance component in a body part as impedance in the body part by impedance component measuring means 21, measures a muscular tissue effective length in the body part by muscular tissue effective length measuring means 22, computes biologically equivalent model parameters including extracellular fluid resistivity and distribution membrane capacitance based on these resistance component, reactance component and muscular tissue effective length by biologically equivalent model parameter computation means 23, and determines a muscle fatigue level based on the ratio of the extracellular fluid resistivity to the distribution membrane capacitance by muscle fatigue level determination means 24.

16 Claims, 8 Drawing Sheets

- 21 IMPEDANCE COMPONENT MEASURING MEANS
- 22 MUSCULAR TISSUE EFFECTIVE LENGTH MEASURING MEANS
- 23 BIOLOGICALLY EQUIVALENT MODEL PARAMETER COMPUTATION MEANS
- 24 MUSCLE FATIGUE LEVEL DETERMINATION MEANS

MUSCLE FATIGUE LEVEL MEASURING DEVICE

BACKGROUND OF THE INVENTION (i) Field of the Invention

The present invention relates to a muscle fatigue level measuring device which estimates the level of fatigue of muscles present in a body part (i.e., muscle fatigue level) based on impedance in the body part.

(ii) Description of the Related Art

Conventional muscle fatigue evaluation devices (muscular fatigue determination devices) place electrodes on a body part so as to measure a change in potential (myoelectric potential) caused by contraction of muscles present in the body part and evaluate (determine) muscle fatigue (muscular fatigue) (for example, refer to Patent Publications 1 and 2).

Patent Publication 1

Japanese Patent Application Laid-Open No. 232/2000

Patent Publication 2

Japanese Patent Application Laid-Open No. 224072/2002

However, the conventional muscle fatigue evaluation devices (muscular fatigue determination devices) have a problem that the electrodes must be placed at the same distance from each other every time the measurement is made because the magnitude of the measured myoelectric potential varies if the distance between the electrodes placed on the body part varies.

Consequently, an object of the present invention is to solve the above problem of the prior art and provide a muscle fatigue level measuring device which estimates a muscle fatigue level without being influenced by a distance between electrodes.

SUMMARY OF THE INVENTION

To achieve the above object, a muscle fatigue level measuring device of the present invention comprises:
impedance component measuring means,
muscular tissue effective length measuring means,
biologically equivalent model parameter computation means, and
muscle fatigue level determination means, wherein
the impedance component measuring means measures a resistance component and a reactance component in a body part as impedance in the body part,
the muscular tissue effective length measuring means measures a muscular tissue effective length in the body part,
the biologically equivalent model parameter computation means computes biologically equivalent model parameters including extracellular fluid resistivity and distribution membrane capacitance based on the resistance component and reactance component measured by the impedance component measuring means and the muscular tissue effective length measured by the muscular tissue effective length measuring means, and
the muscle fatigue level determination means determines a muscle fatigue level based on the ratio between the extracellular fluid resistivity and distribution membrane capacitance computed by the biologically equivalent model parameter computation means.

Further, the impedance component measuring means comprises:
current supply means,
voltage measuring means, and
impedance component computation means, wherein
the current supply means supplies alternating currents of multiple frequencies to a body part,
the voltage measuring means measures voltages generated in the body part by supplying the alternating currents of multiple frequencies by the current supply means, and
the impedance component computation means computes resistance components and reactance components in the body part by dividing the voltages measured by the voltage measuring means by the currents supplied from the current supply means.

Further, the alternating currents of multiple frequencies are an alternating current with a frequency of 50 kHz and an alternating current with a frequency of 6.25 kHz.

Further, the muscular tissue effective length measuring means comprises:
part length measuring means,
part width measuring means, and
muscular tissue effective length computation means, wherein
the part length measuring means measures a part length in the body part,
the part width measuring means measures a part width in the body part, and
the muscular tissue effective length computation means computes the muscular tissue effective length in the body part based on the part length measured by the part length measuring means and the part width measured by the part width measuring means.

Further, the muscular tissue effective length computation means computes the muscular tissue effective length by use of the following expression:

$$Meff = k\sqrt{Ml^2 \times Mw^2}$$

wherein Meff represents the muscular tissue effective length, Ml represents the part length, Mw represents the part width, and k represents a correction coefficient.

Further, the biologically equivalent model parameter computation means computes extracellular fluid resistivity, intracellular fluid resistivity and distribution membrane capacitance as biologically equivalent model parameters by use of the following expressions:

$$(R+jX)/Meff = \rho r + j\rho x$$

wherein R represents the resistance component, jX represents the reactance component, Meff represents the muscular tissue effective length, and $\rho r$ and $j\rho x$ represent a real part and imaginary part of complex resistivity, respectively, $$1/(\rho r + j\rho x) = 1/Re + 1/(Ri + j \times 2\pi \times f \times Cm)$$

wherein Re represents the extracellular fluid resistivity, Ri represents the intracellular fluid resistivity, Cm represents the distribution membrane capacitance, f represents a measuring frequency, j represents an imaginary number, and $\pi$ represents a pi.

Further, the muscle fatigue level determination means computes the muscle fatigue level by dividing the extracellular fluid resistivity by the distribution membrane capacitance.

Further, the muscle fatigue level determination means further computes a more accurate muscle fatigue level by considering at least one of personal data including a body weight, a body height, age and sex in addition to the computed muscle fatigue level.

Further, the muscle fatigue level measuring device of the present invention comprises:
a main body,
first ranging portions,
second ranging portions, and
electrode sets, wherein
the main body serves as a base,
the first ranging portions are disposed on the main body such that they can slide freely in a part width direction in a body part so as to measure a part width,
the second ranging portions are disposed on the first ranging portions such that they can slide freely in a part length direction in the body part so as to measure a part length, and
the electrode sets comprise current-carrying electrodes and measuring electrodes which are disposed at positions on the second ranging portions which correspond to the part length,
the impedance component measuring means includes the electrode sets and measures a resistance component and a reactance component in a body part which is in direct contact with the electrode sets as impedance in the body part, and
the muscular tissue effective length measuring means computes a muscular tissue effective length in the body part based on the part width measured by the first ranging portions and the part length measured by the second ranging portions.

Further, the electrode sets are disposed at the positions on the second ranging portions which correspond to the part length via flexible, elastic members.

Figures 1, 2:
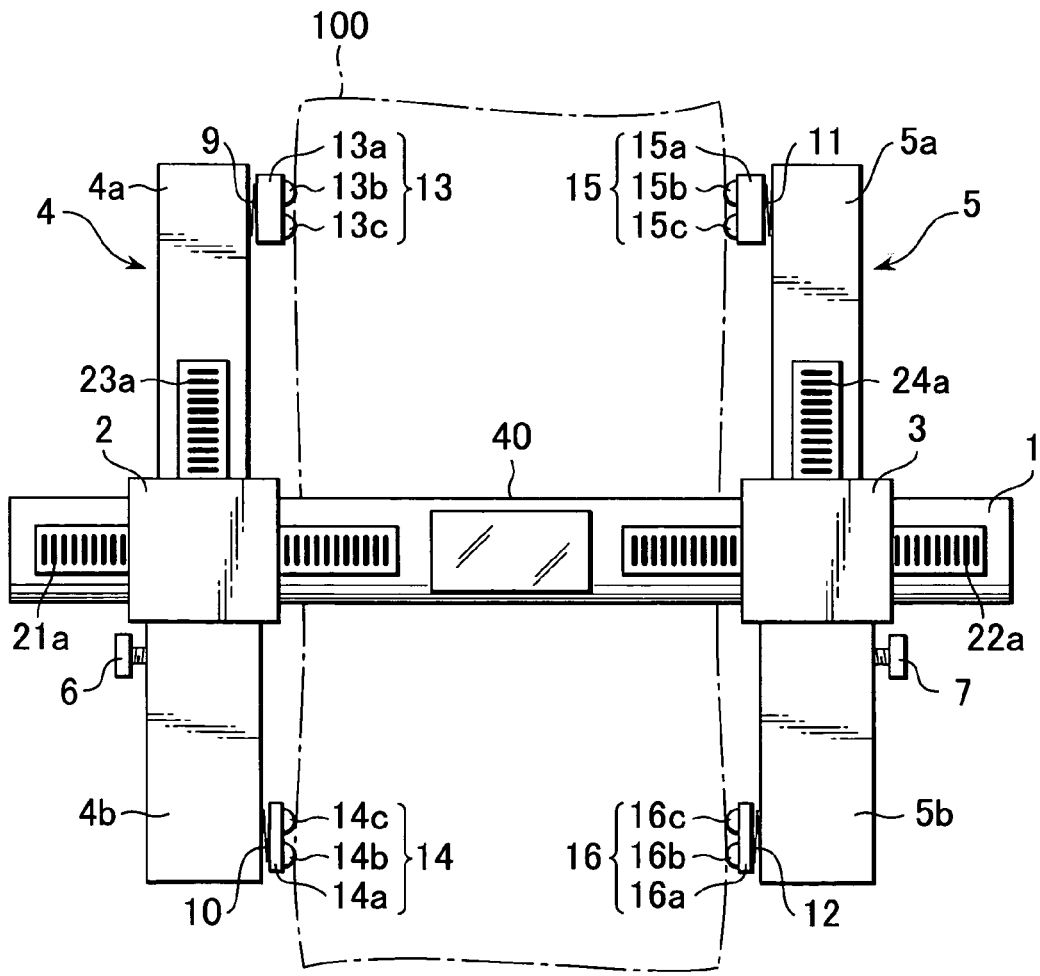
FIG. 1 is a block diagram showing a functional constitution of a muscle fatigue level measuring device according to the present invention.
FIG. 2 is a front view of the muscle fatigue level measuring device at the time of measurement.

Reference numeral 1 denotes a main body; 2 and 3 denote first ranging portions; 4 (4a, 4b) and 5 (5a, 5b) denote second ranging portions; 13b, 14b, 15b, and 16b denote current-carrying electrodes; 13c, 14c, 15c, and 16c denote measuring electrodes; 21 denotes impedance component measuring means; 22 denotes muscular tissue effective length measuring means; 23 denotes biologically equivalent model parameter computation means; 24 denotes muscle fatigue level determination means; and 100 denotes a body.

DETAILED DESCRIPTION OF THE PREFERRED EMBODIMENTS

Hereinafter, an embodiment of the present invention will be described by use of the drawings.

Figure 3:
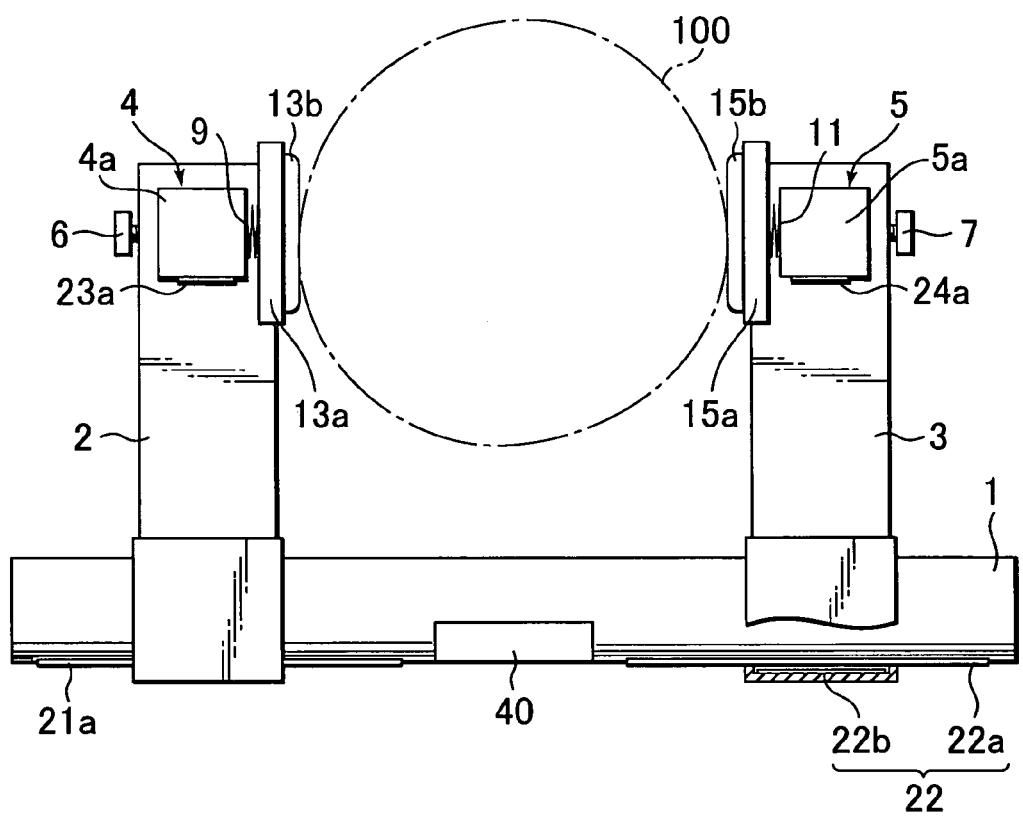
FIG. 3 is a plan view of the muscle fatigue level measuring device at the time of measurement.
Figure 4:
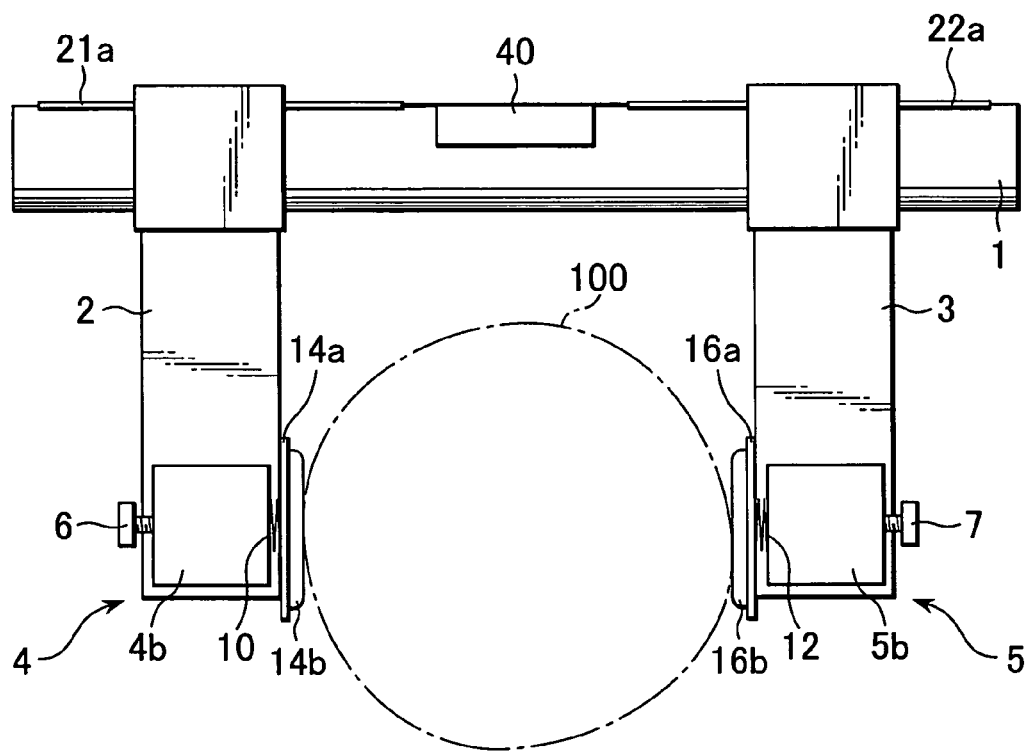
FIG. 4 is a bottom view of the muscle fatigue level measuring device at the time of measurement.
Figure 5:
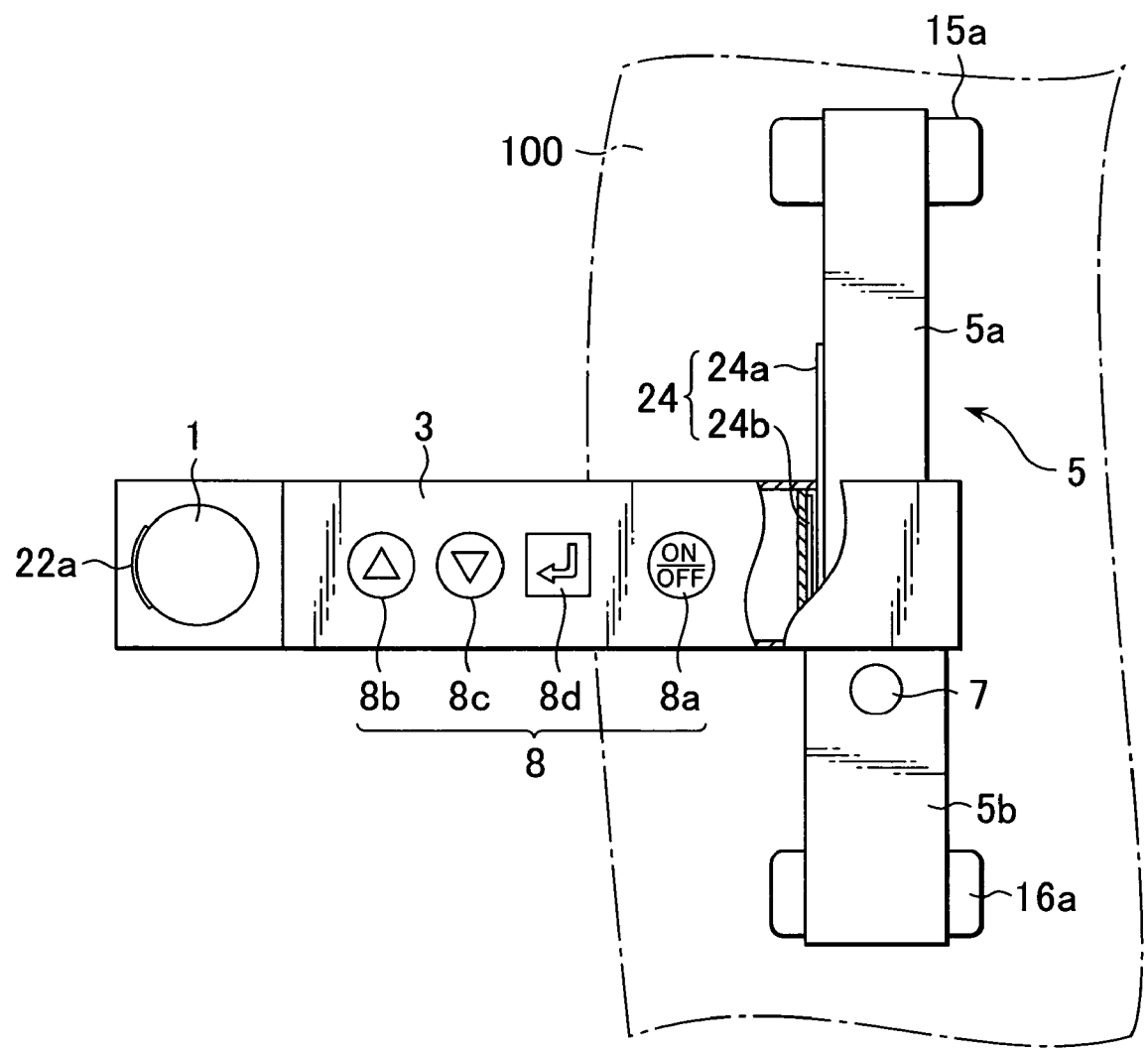
FIG. 5 is a right side view of the muscle fatigue level measuring device at the time of measurement.
Figure 6:
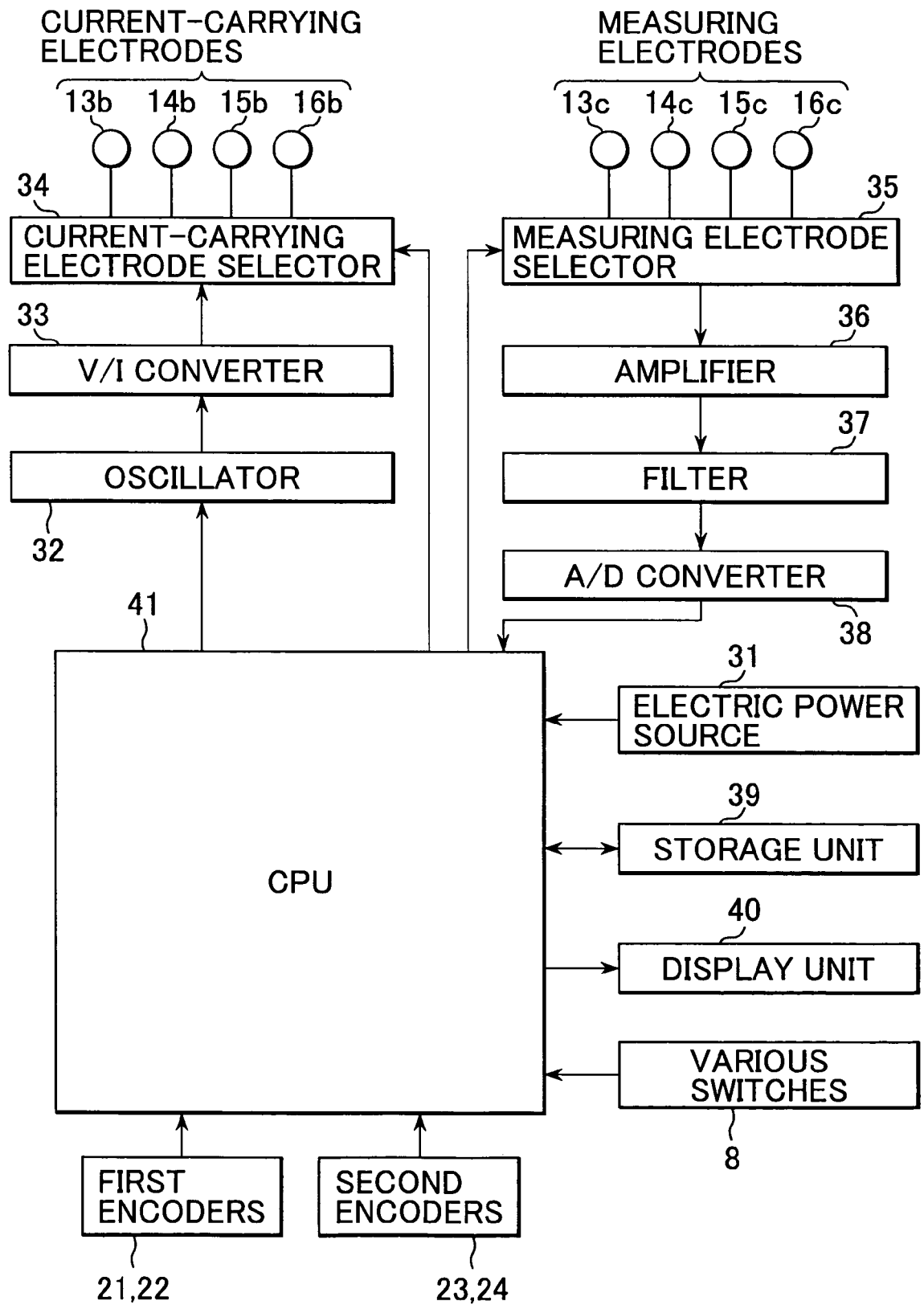
FIG. 6 is a block diagram showing a structural constitution of the muscle fatigue level measuring device according to the present invention.
Figure 10:
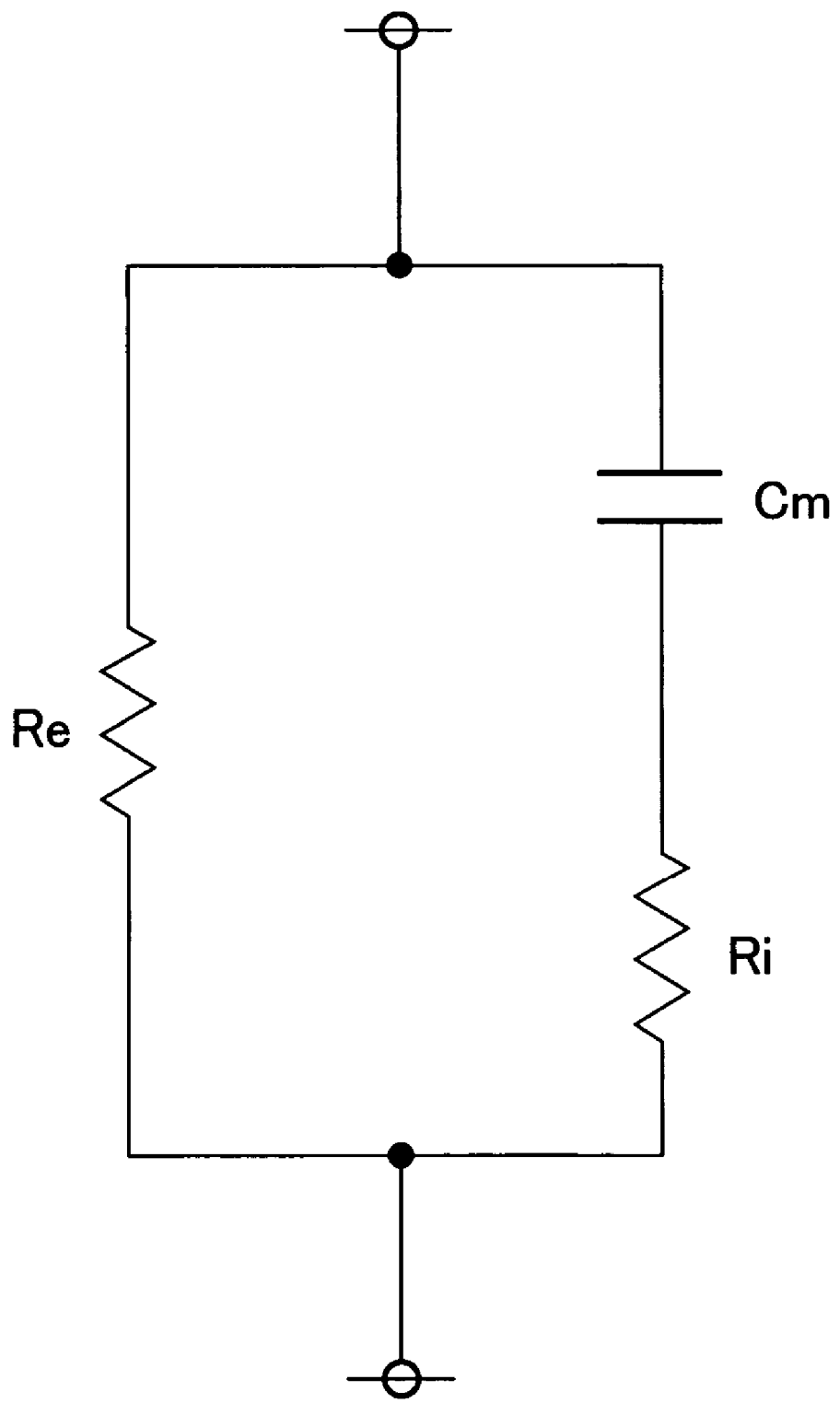
FIG. 10 is a biologically equivalent model.

Firstly, the constitution of a muscle fatigue level measuring device according to the present invention will be described in detail with reference to a functional block diagram shown in FIG. 1, a front view of the device at the time of measurement which is shown in FIG. 2, a plan view thereof which is shown in FIG. 3, a bottom view thereof which is shown in FIG. 4, a right side view thereof which is shown in FIG. 5, a structural block diagram shown in FIG. 6 and a biologically equivalent model shown in FIG. 10. The outer shape of the muscle fatigue level measuring device of the present invention is roughly formed by a main body 1, first ranging portions 2 and 3, and second ranging portions 4 and 5 (4a and 4b, and 5a and 5b).

The main body 1 constitutes the base of the present device and has a cylindrical shape. It incorporates an electronic circuit board on which an electric power source 31, an oscillator 32, a V/I converter 33, a current-carrying electrode selector 34, a measuring electrode selector 35, an amplifier 36, a filter 37, an A/D converter 38, a storage unit 39, a display unit 40 and a CPU 41 are mounted.

The first ranging portions 2 and 3 serve as jaws for measuring a part width in a body part and each have a prismatic shape. The portions 2 and 3 are attached to the main body 1 such that they can slide freely along the direction of the cylinder axis of the main body 1 (or the direction of the part width in the body part) and extend in a direction perpendicular to the cylinder axis direction of the main body 1 (or the direction of the part width in the body part).

Further, first electrodes 21a and 22a are provided on the guide surface of the main body 1, and second electrodes 21b and 22b are provided on the guide surfaces of the first ranging portions 2 and 3. These first electrodes 21a and 22a and second electrodes 21b and 22b form first encoders 21 and 22. Just like known electronic slide calipers, they detect relative displacement magnitudes between the main body 1 and the first ranging portions 2 and 3 and output the data to the CPU 41.

The second ranging portions 4 and 5 serve as jaws for measuring a part length in a body part and comprise a pair of prismatic members 4a and 4b and a pair of prismatic members 5a and 5b, respectively. The members 4a and 5a are attached to the members 4b and 5b such that the members 4a and 5a can slide freely inside the members 4b and 5b, respectively. The second ranging portions 4 and 5 are disposed at the front ends of the first ranging portions 2 and 3 such that the prismatic members 4a and 5a slide in a direction perpendicular to the cylinder axis direction of the main body 1 and the prism axis directions of the first ranging portions 2 and 3 (or the direction of the part length in the body part).

Further, third electrodes 23a and 24a are provided on the guide surfaces of the prismatic members 4a and 5a, and fourth electrodes 23b (not shown) and 24b are provided on the guide surfaces of the prismatic members 4b and 5b. These third electrodes 23a and 24a and fourth electrodes 23b and 24b form second encoders 23 and 24. Just like known electronic slide calipers, they detect relative displacement magnitudes between the prismatic members 4a and 5a and the prismatic members 4b and 5b and output the data to the CPU 41.

In addition, the second ranging portion 4 has an adjustment screw 6, and the second ranging portion 5 has an adjustment screw 7 and various switches 8. The adjustment screws 6 and 7 fit screw grooves formed in the prismatic members 4b and 5b and press the prismatic members 4a and 5a through the prismatic members 4b and 5b so as to fix the positions of the prismatic members 4a and 5a and the prismatic members 4b and 5b when the prismatic members 4a and 5a slide within the prismatic members 4b and 5b. The switches 8 comprise an ON/OFF switch 8a which switches between supplying electric power to units in the electrical system and stopping supplying the electric power to the units, an UP switch 8b which increases a numerical value displayed on the display unit 40 at the time of setting of various data such as personal data (e.g., a body weight, a body height, age and sex), a DOWN switch 8c which decreases a numerical value displayed on the display unit 40 at the time of setting of various data such as personal data (e.g., a body weight, a body height, age and sex), and a SET switch 8d which sets a numerical value selected by use of the UP switch 8b or the DOWN switch 8c.

Further, at the front ends of the prismatic members 4a, 5a, 4b and 5b of the second ranging portions 4 and 5, electrode sets are disposed via springs 9, 10, 11 and 12 such that they face inward in the cylinder axis direction of the main body 1. The electrode sets comprise plates 13a, 14a, 15a and 16a, current-carrying electrodes 13b, 14b, 15b and 16b, and measuring electrodes 13c, 14c, 15c and 16c. These electrodes are placed on the corresponding plates.

Further, the oscillator 32 generates constant voltages of different frequencies (50 kHz and 6.25 kHz). The V/I converter 33 receives the constant voltages generated from the oscillator 32, converts the constant voltages to constant currents and outputs the constant currents. The current-carrying electrode selector 34 receives the constant currents output from the V/I converter 33 and outputs the constant currents to the given current-carrying electrodes 13b and 16b or 14b and 15b. Further, the current-carrying electrodes 13b, 14b, 15b and 16b serve as communication ports for passing the constant currents supplied from the current-carrying electrode selector 34 through a body part. The oscillator 32, the V/I converter 33, the current-carrying electrode selector 34 and the current-carrying electrodes 13b, 14b, 15b and 16b constitute current supply means for supplying alternating currents of multiple frequencies (50 kHz and 6.25 kHz) through a body part.

Further, the measuring electrodes 13c, 14c, 15c and 16c serve as communication ports for detecting voltages caused by impedance in the body part when the currents are passed through the body part from the current-carrying electrodes 13b, 14b, 15b and 16b. The measuring electrode selector 35 receives the voltages from the given measuring electrodes 14c and 15c, 13c and 16c and outputs the voltages. The amplifier 36 receives the voltages caused by the impedance in the body part from the measuring electrode selector 35 and amplifies and outputs the voltages. The filter 37 receives the voltages from the amplifier 36 and allows only specific frequency components (50 kHz and 6.25 kHz) to pass therethrough. The A/D converter 38 converts the voltages having passed through the filter 37 from analog signals to digital signals and outputs the digital signals to the CPU 41. These measuring electrodes 13c, 14c, 15c and 16c, the measuring electrode selector 35, the amplifier 36, the filter 37 and the A/D converter 38 constitute voltage measuring means for measuring voltages of alternating currents of multiple frequencies (50 kHz and 6.25 kHz) occurring in a body part.

Further, the storage unit 39 stores various setting data set by means of the SET switch 8d, and the display unit 40 displays various setting data and various measurement data.

Further, the CPU 41 serves as impedance component computation means, part width computation means, part length computation means, muscular tissue effective length computation means, biologically equivalent model parameter computation means 23, and muscle fatigue level determination means 24. The CPU 41 also controls units in the electrical system and performs computations in a known manner.

The impedance component computation means divides the voltages of alternating currents of multiple frequencies (50 kHz and 6.25 kHz) received from the A/D converter 38 by the currents passing through the body part from the current supply means so as to compute a resistance component and a reactance component in the body part for each frequency (i.e., 50 kHz and 6.25 kHz). The above current supply means, voltage measuring means and impedance component computation means constitute impedance component measuring means 21 for measuring a resistance component and a reactance component in a body part as impedance in the body part.

The part width computation means computes a part width Mw based on outputs received from the first encoders 21 and 22, and the part length computation means computes a part length Ml based on outputs received from the second encoders 23 and 24. The muscular tissue effective length computation means substitutes the part width Mw computed by the part width computation means and the part length Ml computed by the part length computation means into an expression 7 so as to compute a muscular tissue effective length Meff in the body part.

$$Meff = k \sqrt{Ml^2 \times Mw^2}$$

wherein k is a correction coefficient (e.g., $\frac{1}{2}^{1/2}$ which is experimentally predetermined).

The above main body 1, first ranging portions 2 and 3 and part width computation means constitute part width measuring means for measuring a part width Mw in a body part. Further, the above second ranging portions 4 and 5 and part length computation means constitute part length measuring means for measuring a part length Ml in a body part. Further, the above part width measuring means, part length measuring means and muscular tissue effective length computation means constitute muscular tissue effective length measuring means 22 for measuring a muscular tissue effective length in a body part.

The biologically equivalent model parameter computation means 23 substitutes the resistance component R and the reactance component jX which have been computed for each frequency (50 kHz and 6.25 kHz) by the impedance component computation means and the muscular tissue effective length Meff which has been computed by the muscular tissue effective length computation means into an expression 8 for each frequency (50 kHz and 6.25 kHz) so as to compute a real part ρr and imaginary part jρx of complex resistivity for each frequency (50 kHz and 6.25 kHz).

$$(R+jX)/Meff = \rho r + j\rho x$$

Further, the biologically equivalent model parameter computation means 23 substitutes the real part ρr and imaginary part jρx of complex resistivity which have been computed for each frequency (50 kHz and 6.25 kHz), a measuring frequency f, an imaginary number j and a pi π into an expression 9 for each frequency, and three equations are established based on the expression for each frequency (50 kHz and 6.25 kHz) so as to compute extracellular fluid resistivity Re, intracellular fluid resistivity Ri and distribution membrane capacitance Cm. The extracellular fluid resistivity Re, intracellular fluid resistivity Ri or distribution membrane capacitance Cm is called a biologically equivalent model parameter.

$$1/(\rho r + j\rho x) = 1/Re + 1/(Ri + j \times 2\pi f \times Cm)$$

The muscle fatigue level determination means 24 divides the extracellular fluid resistivity Re which has been computed by the biologically equivalent model parameter computation means 23 by the distribution membrane capacitance Cm so as to compute (determine) a muscle fatigue level K. Then, the muscle fatigue level determination means substitutes the computed muscle fatigue level K and personal data (body weight W, body height H, age Ag and sex S) set by the SET switch 8d into an expression 10 so as to compute (determine) a more accurate muscle fatigue level Kh.

$$Kh = K \times f1(W) \times f2(H) \times f3(Ag) \times f4(S)$$

wherein functions f1, f2, f3 and f4 are functions derived in advance from data collected from a number of subjects.

Figure 7:
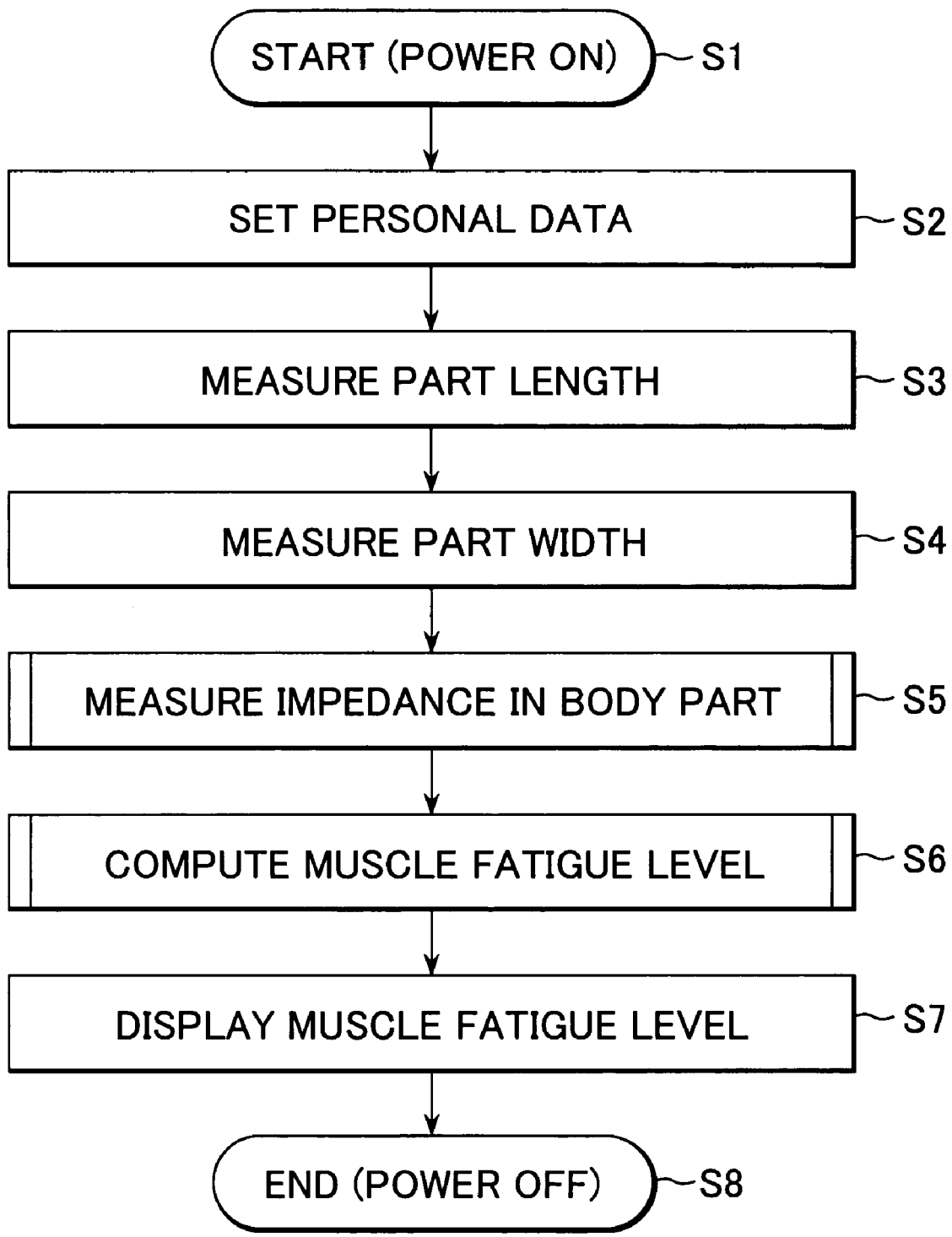
FIG. 7 is a main flowchart showing the procedure for using the muscle fatigue level measuring device according to the present invention and the operation of the device.
Figure 8:
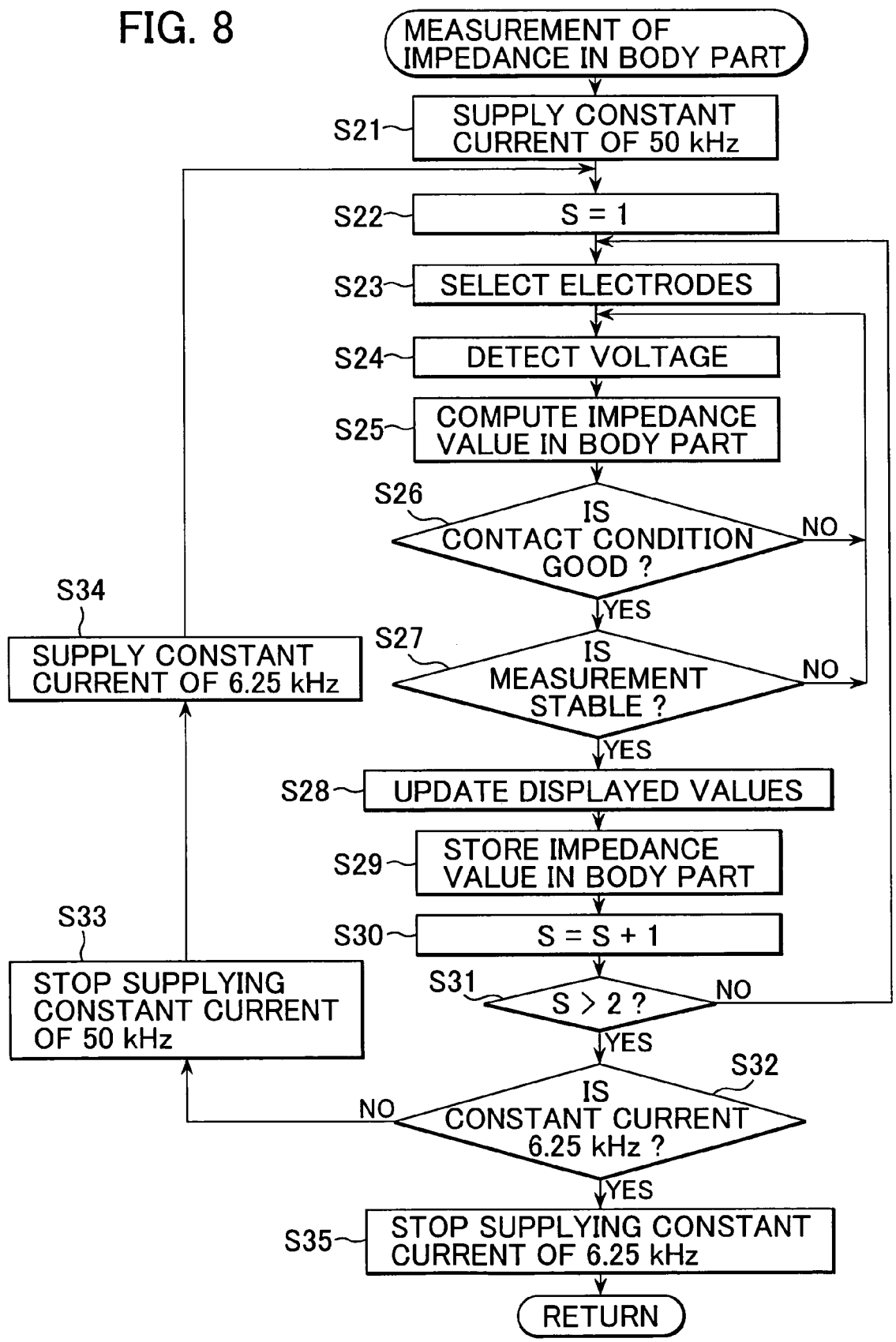
FIG. 8 is a subroutine flowchart showing steps for measuring impedance in a body part.
Figure 9:
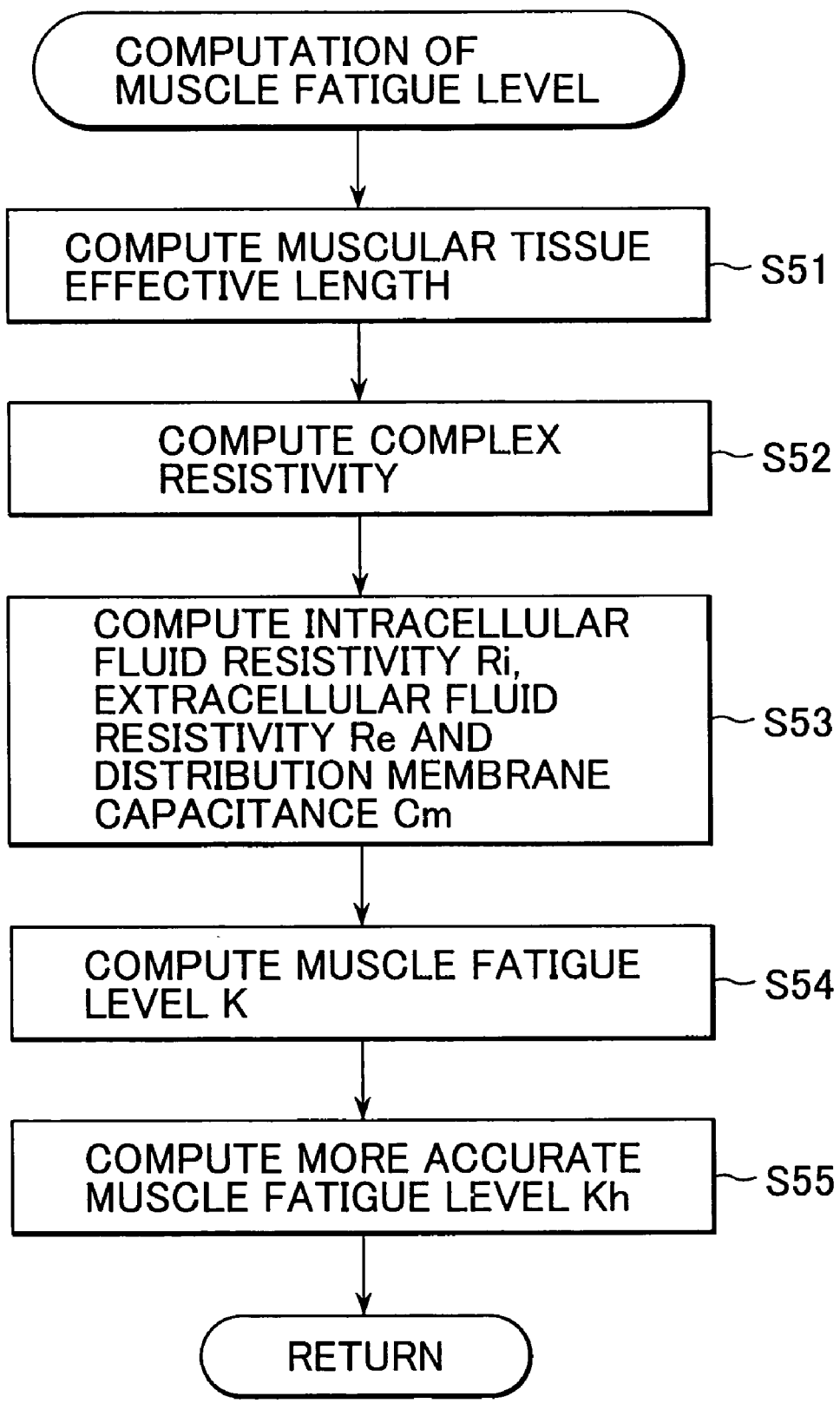
FIG. 9 is a subroutine flowchart showing steps for determining a muscle fatigue level in a body part.

Next, the procedure for using the muscle fatigue level measuring device according to the present invention and the operation of the device will be specifically described with reference to a main flowchart shown in FIG. 7, a subroutine flowchart of measurement of impedance in a body part which is shown in FIG. 8, and a subroutine flowchart of determination of a muscle fatigue level in a body part which is shown in FIG. 9.

Firstly, at the press of the ON/OFF switch 8a, electric power is supplied to units in the electrical system from the electric power source 31 (STEP S1).

Then, numeric values corresponding to personal data (body weight, body height, age and sex) are selected by the UP switch 8b or the DOWN switch 8c. Once the numeric values are set by the SET switch 8d, the set personal data (body weight, body height, age and sex) are stored in the storage unit 39 (STEP S2).

Then, after the relative positions of the prismatic members 4a and 5a and prismatic members 4b and 5b of the second ranging portions are determined and fixed by the adjustment screws 6 and 7, the second encoders 23 and 24 detect relative displacement magnitudes between the prismatic members 4a and 5a and the prismatic members 4b and 5b. The CPU (part length computation means) 41 computes an average (part length Ml) of a distance between the electrode sets 13 and 14 and a distance between the electrode sets 15 and 16 of the second ranging portions based on the detected relative displacement magnitudes (STEP S3).

Then, the electrodes 13b, 13c, 14b, 14c, 15b, 15c, 16b and 16c are brought into direct contact with a body part whose muscle fatigue level is desired to be determined by adjusting a distance between the first ranging portions 2 and 3. Then, the first encoders 21 and 22 detect relative displacement magnitudes between the main body 1 and the first ranging portions 2 and 3. The CPU (part width computation means) 41 computes a distance (part width Mw) between the electrode sets 13 (14) and 15 (16) based on the detected relative displacement magnitudes (STEP S4).

Then, impedance in the body part is measured (STEP S5). To state more specifically, the oscillator 32 generates a constant voltage of 50 kHz under the control of the CPU 41. Receiving the constant voltage, the V/I converter 33 changes the constant voltage to a constant current and outputs the constant current (STEP S21). Then, S=1 is registered in a register (STEP S22).

Then, under the control of the CPU 41, the current-carrying electrode selector 34 selects the current-carrying electrodes 13b and 16b, and the measuring electrode selector 35 selects the measuring electrodes 14c and 15c (STEP S23). Then, the constant current output from the V/I converter 33 passes through the body part situated between the current-carrying electrodes 13b and 16, and at that time, the measuring electrodes 14c and 15c detect a voltage produced in the body part (STEP S24).

Receiving the detected voltage, the amplifier 36 amplifies and outputs the detected voltage. Receiving the amplified voltage, the filter 37 allows only a frequency component corresponding to 50 kHz to pass therethrough. Then, on the receipt of the voltage of 50 kHz, the A/D converter 38 converts the analog signal to a digital signal and outputs the digital signal. Receiving the digital signal, the CPU (impedance component computation means) 41 computes a resistance component and a reactance component in the body part by dividing the voltage of 50 kHz by the current passing through the body part from the current supply means (STEP S25).

Then, it is determined based on the variations of the resistance and reactance components in the body part whether the condition of contact between the electrodes and the body part are good (STEP S26). When the variations are higher than given values, it is determined that the contact condition is not good, and STEPS S24 and S25 are carried out again (NO in STEP S26). Meanwhile, when the variations are lower than or equal to the given values, it is determined that the contact condition is good, and the subsequent step is carried out (YES in STEP S26).

Then, it is determined whether the measurement is stable or not, based on continuation of the variations of the resistance and reactance components in the body part which are lower than or equal to the given values (STEP S27). When the variations lower than or equal to the given values are not continued over a given time, it is determined that the measurement is not stable, and STEPS S24 to S26 are carried out again (NO in STEP S27). Meanwhile, when the variations lower than or equal to the given values are continued over the given time, it is determined that the measurement is stable, and the subsequent step is carried out (YES in STEP S27).

Then, values displayed on the screen of the display unit 40 are updated with values of the resistance and reactance values in the body part when the measurement is determined to be stable (STEP S28), and the values of the resistance and reactance values in the body part when the measurement is determined to be stable are stored in the storage unit 39 (STEP S29).

Then, the register increases the currently registered value S by 1 and registers the updated value S (STEP S30) and determines whether the updated S is larger than 2 or not (STEP S31). When S is not larger than 2, STEPS S23 to S30 are carried out again (NO in STEP S31). In STEP S23 in this case, the current-carrying electrode selector 34 selects the current-carrying electrodes 14b and 15b, and the measuring electrode selector 35 selects the measuring electrodes 13c and 16c, under the control of the CPU 41. Meanwhile, when S is larger than 2, the subsequent step is carried out (YES in STEP S31).

Then, it is determined whether a constant current passing through the body part is 6.25 kHz (i.e., whether a constant voltage generated by the oscillator is 6.25 kHz) (STEP S32). When it is not 6.25 kHz (NO in STEP S32), generation of constant voltage of 50 kHz by the oscillator 32 under the control of the CPU 41 is stopped (STEP S33), a constant voltage of 6.25 kHz is generated (i.e., a constant current of 6.25 kHz is passed through the body part), and STEP S22 and subsequent steps thereof are carried out again (STEP S34). Meanwhile, when it is 6.25 kHz (YES in STEP S32), generation of the constant voltage of 6.25 kHz by the oscillator 32 under the control of the CPU 41 is stopped (STEP S33), and the measurement of the impedance in the body part is terminated (STEP S35).

Then, a muscle fatigue level is computed (STEP S6). To be more specific, the CPU (muscular tissue effective length computation means) 41 substitutes the part length Ml computed in STEP S3 and the part width Mw computed in STEP S4 into the expression 7 so as to compute a muscular tissue effective length Meff in the body part (STEP S51).

Then, the CPU (biologically equivalent model parameter computation means 23) 41 substitutes the muscular tissue effective length Meff, the resistance component R and reactance component jX at the time of measurement at 50 kHz stored in the storage unit 39, and a resistance component R and reactance component jX at the time of measurement at 6.25 kHz into the expression 8 so as to compute a real part ρr and imaginary part jρx of complex resistivity at the time of measurement at 50 kHz and a real part ρr and imaginary part jρx of complex resistivity at the time of measurement at 6.25 kHz (STEP S52).

Then, based on a first expression resulting from substitution of the real part ρr and imaginary part jρx of the complex resistivity at the time of measurement at 50 kHz, an imaginary number j and a pi π into the expression 9 and a second expression resulting from substitution of the real part ρr and imaginary part jρx of the complex resistivity at the time of measurement at 6.25 kHz, an imaginary number j and a pi π into the expression 9, the CPU (biologically equivalent model parameter computation means 23) 41 establishes three equations excluding the imaginary part jρx of the complex resistivity in the second expression so as to compute extracellular fluid resistivity Re, intracellular fluid resistivity Ri and distribution membrane capacitance Cm as biologically equivalent model parameters (STEP S53).

Then, out of these biologically equivalent model parameters, the CPU (muscle fatigue level determination means 24) 41 divides the extracellular fluid resistivity Re by the distribution membrane capacitance Cm so as to compute (determine) a muscle fatigue level K (STEP S54). Then, the CPU (muscle fatigue level determination means 24) 41 substitutes the muscle fatigue level K and the personal data (body weight, body height, age and sex) set in STEP S2 into the expression 10 so as to compute (determine) a more accurate muscle fatigue level Kh, whereby the computation of the muscle fatigue level is completed (STEP S55).

Then, the display unit 40 displays the muscle fatigue level K or more accurate muscle fatigue level Kh on the screen (STEP S7). At the press of the ON/OFF switch 8a, the power source 31 stops supplying electric power to the units in the electrical system, whereby a series of procedural steps of the present device are completed (STEP S8).

As described above, the muscle fatigue level measuring device of the present invention measures a resistance component and a reactance component in a body part as impedance in the body part by the impedance component measuring means 21, measures a muscular tissue effective length in the body part by the muscular tissue effective length measuring means 22, computes biologically equivalent model parameters including extracellular fluid resistivity and distribution membrane capacitance based on these resistance component, reactance component and muscular tissue effective length by biologically equivalent model parameter computation means 23, and determines a muscle fatigue level based on the ratio of the extracellular fluid resistivity to the distribution membrane capacitance by the muscle fatigue level determination means 24. Thus, the muscle fatigue level measuring device of the present invention can obtain a muscle fatigue level with high accuracy since it obtains the muscle fatigue level in consideration of the muscular tissue effective length in the body part which is a distance between the electrodes.

Further, data serving as a basis for computing the muscular tissue effective length in the body part can be obtained by the first ranging portions 2 and 3 for measuring a part width which are disposed on the main body 1 such that they can slide freely in a part width direction in a body part and the second ranging portions 4 and 5 for measuring a part length which are disposed on the first ranging portions 2 and 3 such that they can slide freely in a path length direction in the body part. Thereby, the measurement can be made more easily and more accurately.

In the above description, springs were used between the electrode sets and the second ranging portions so as to have the electrodes contact with the body part in good condition. However, the present invention can also be practiced by using rubber or other flexible, elastic members in place of the springs.

As described above, the muscle fatigue level measuring device of the present invention has the muscular tissue effective length measuring means by which the device can obtain a muscle fatigue level in consideration of muscular tissue effective length in a body part. Thus, the obtained muscle fatigue level is highly accurate.

Further, the muscle fatigue level measuring device of the present invention measures a part width and a part length by the main body, first ranging portions and second ranging portions constituted such that distances in a body part can be changed so as to obtain a muscular tissue effective length in the body part. Thus, the muscle fatigue level can be obtained more easily and more accurately.

Further, it can also be easily achieved to increase accuracy by use of conventionally used electromyography in combination with the present invention.

What is claimed is:

1. A muscle fatigue level measuring device comprising:
impedance component measuring means,
muscular tissue effective length measuring means
biologically equivalent model parameter computation means, and
muscle fatigue level determination means,
wherein
the impedance component measuring means measures a resistance component and a reactance component in a body part as impedance in the body part,
the muscular tissue effective length measuring means measures a muscular tissue effective length in the body part,
the biologically equivalent model parameter computation means computes biologically equivalent model parameters including extracellular fluid resistivity and distribution membrane capacitance based on the resistance component and reactance component measured by the impedance component measuring means and the muscular tissue effective length measured by the muscular tissue effective length measuring means, and the muscle fatigue level determination means determines a muscle fatigue level based on the ratio between the extracellular fluid resistivity and distribution membrane capacitance computed by the biologically equivalent model parameter computation means.

2. The device of claim 1, wherein the impedance component measuring means comprises:

current supply means, voltage measuring means, and impedance component computation means, wherein the current supply means supplies alternating currents of multiple frequencies to a body part, the voltage measuring means measures voltages generated in the body part by supplying the alternating currents of multiple frequencies by the current supply means, and the impedance component computation means computes resistance components and reactance components in the body part by dividing the voltages measured by the voltage measuring means by the currents supplied from the current supply means.

3. The device of claim 2, wherein the alternating currents of multiple frequencies are an alternating current with a frequency of 50 kHz and an alternating current with a frequency of 6.25 kHz.

4. The device of claim 1, wherein the muscular tissue effective length measuring means comprises:

part length measuring means, part width measuring means, and muscular tissue effective length computation means, wherein the part length measuring means measures a part length in the body part, the part width measuring means measures a part width in the body part, and the muscular tissue effective length computation means computes the muscular tissue effective length in the body part based on the part length measured by the part length measuring means and the part width measured by the part width measuring means.

5. The device of claim 2, wherein the muscular tissue effective length measuring means comprises:

part length measuring means, part width measuring means, and muscular tissue effective length computation means, wherein the part length measuring means measures a part length in the body part, the part width measuring means measures a part width in the body part, and the muscular tissue effective length computation means computes the muscular tissue effective length in the body part based on the part length measured by the part length measuring means and the part width measured by the part width measuring means.

6. The device of claim 3, wherein the muscular tissue effective length measuring means comprises:

part length measuring means, part width measuring means, and muscular tissue effective length computation means, wherein the part length measuring means measures a part length in the body part, the part width measuring means measures a part width in the body part, and the muscular tissue effective length computation means computes the muscular tissue effective length in the body part based on the part length measured by the part length measuring means and the part width measured by the part width measuring means.

7. The device of claim 4, wherein the muscular tissue effective length computation means computes the muscular tissue effective length by use of the following expression:

$$Meff = k\sqrt{Ml^2 \times Mw^2}$$

wherein Meff represents the muscular tissue effective length, Ml represents the part length, Mw represents the part width, and k represents a correction coefficient.

8. The device of claim 5, wherein the muscular tissue effective length computation means computes the muscular tissue effective length by use of the following expression:

$$Meff = k\sqrt{Ml^2 \times Mw^2}$$

wherein Meff represents the muscular tissue effective length, Ml represents the part length, Mw represents the part width, and k represents a correction coefficient.

9. The device of claim 6, wherein the muscular tissue effective length computation means computes the muscular tissue effective length by use of the following expression:

$$Meff = k\sqrt{Ml^2 \times Mw^2}$$

wherein Meff represents the muscular tissue effective length,

Ml represents the part length, Mw represents the part width, and k represents a correction coefficient.

10. The device of any one of claims 1 to 9, wherein the biologically equivalent model parameter computation means computes extracellular fluid resistivity, intracellular fluid resistivity and distribution membrane capacitance as biologically equivalent model parameters by use of the following expressions:

$$(R+jX)/Meff = \rho r + j\rho x$$

wherein R represents the resistance component, jX represents the reactance component, Meff represents the muscular tissue effective length, and ρr and jρx represent a real part and imaginary part of complex resistivity, respectively, $$1/(\rho r + j\rho x) = 1/Re + 1/(Ri + j \times 2\pi \times f \times Cm)$$

wherein Re represents the extracellular fluid resistivity, Ri represents the intracellular fluid resistivity, Cm represents the distribution membrane capacitance, f represents a measuring frequency, j represents an imaginary number, and π represents a pi.

11. The device of any one of claims 1 to 9, wherein the muscle fatigue level determination means computes the muscle fatigue level by dividing the extracellular fluid resistivity by the distribution membrane capacitance.

12. The device of claim 10, wherein the muscle fatigue level determination means computes the muscle fatigue level by dividing the extracellular fluid resistivity by the distribution membrane capacitance.

13. The device of claim 11, wherein the muscle fatigue level determination means further computes a more accurate muscle fatigue level by considering at least one of personal data including a body weight, a body height, age and sex in addition to the computed muscle fatigue level.

14. The device of claim 12, wherein the muscle fatigue level determination means further computes a more accurate muscle fatigue level by considering at least one of personal data including a body weight, a body height, age and sex in addition to the computed muscle fatigue level.

15. The device of claim 1, comprising:
a main body,
first ranging portions,
second ranging portions, and
electrode sets,
wherein
the main body serves as a base,
the first ranging portions are disposed on the main body such that they can slide freely in a part width direction in a body part so as to measure a part width,
the second ranging portions are disposed on the first ranging portions such that they can slide freely in a part length direction in the body part so as to measure a part length, and
the electrode sets comprise current-carrying electrodes and measuring electrodes which are disposed at positions on the second ranging portions which correspond to the part length,
the impedance component measuring means includes the electrode sets and measures a resistance component and a reactance component in a body part which is in direct contact with the electrode sets as impedance in the body part, and
the muscular tissue effective length measuring means computes a muscular tissue effective length in the body part based on the part width measured by the first ranging portions and the part length measured by the second ranging portions.

16. The device of claim 15, wherein the electrode sets are disposed at the positions on the second ranging portions which correspond to the part length via flexible, elastic members.

* * * * *